US011801146B2

(12) United States Patent
Chang et al.

(10) Patent No.: US 11,801,146 B2
(45) Date of Patent: Oct. 31, 2023

(54) ARTIFICIAL INTERVERTEBRAL DISC

(71) Applicant: INDUSTRIAL TECHNOLOGY RESEARCH INSTITUTE, Hsinchu (TW)

(72) Inventors: Fang-Chieh Chang, Keelung (TW); Pei-I Tsai, Hsinchu (TW); Shih-Ping Lin, Kaohsiung (TW); Ming-Jun Li, New Taipei (TW); Chih-Chieh Huang, Miaoli County (TW); Hsin-Hsin Shen, Hsinchu County (TW); Meng-Huang Wu, Taipei (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 0 days.

(21) Appl. No.: 17/550,889

(22) Filed: Dec. 14, 2021

(65) Prior Publication Data
US 2023/0172720 A1    Jun. 8, 2023

(30) Foreign Application Priority Data
Dec. 3, 2021 (TW) ................ 110145176

(51) Int. Cl.
*A61F 2/44* (2006.01)
*A61F 2/30* (2006.01)

(52) U.S. Cl.
CPC ........ *A61F 2/4425* (2013.01); *A61F 2/30771* (2013.01); *A61F 2002/30326* (2013.01);
(Continued)

(58) Field of Classification Search
CPC .......... A61F 2002/443; A61F 2/4425
(Continued)

(56) References Cited

U.S. PATENT DOCUMENTS 7,749,272 B2   7/2010  Robie et al.
8,038,716 B2  10/2011  Duggal et al.
(Continued)

FOREIGN PATENT DOCUMENTS

CN    101022770 A    8/2007
CN    204072392 U    1/2015
(Continued)

OTHER PUBLICATIONS

Nassau, Christopher John et al., Analysis of spinal lumbar interbody fusion cage subsidence using Taguchi method, finite element analysis, and artificial neural network, Depart of Mechanical and Aerospace Engineering, University of Missouri, May 2012, 7(3): 247-255.
(Continued)

*Primary Examiner* — Jan Christopher L Merene
(74) *Attorney, Agent, or Firm* — Maschoff Brennan

(57) ABSTRACT

An artificial intervertebral disc is configured to be inserted between adjacent human vertebrae. The artificial intervertebral disc includes a first connection block, a joint block and a second connection block. The joint block has a convex surface and a rear surface. The rear surface of the joint block is stacked on the first connection block. The second connection block is slidably stacked on the convex surface of the joint block, such that the second connection block is movable relative to the first connection block. In addition, the convex surface is a curved surface, and the convex surface is arranged off-axis with respect to the rear surface.

16 Claims, 12 Drawing Sheets

(52) U.S. Cl.
CPC ............... *A61F 2002/30354* (2013.01); *A61F 2002/30599* (2013.01); *A61F 2002/30784* (2013.01); *A61F 2002/443* (2013.01)

(58) Field of Classification Search
USPC .......................................... 623/17.14, 17.15
See application file for complete search history.

(56) References Cited

U.S. PATENT DOCUMENTS

| | | | |
|---|---|---|---|
| 8,998,989 B2 | 4/2015 | Kim et al. | |
| 9,265,618 B2* | 2/2016 | Rashbaum | A61F 2/4611 |
| 9,289,310 B2* | 3/2016 | Chaput | A61B 17/686 |
| 9,510,953 B2 | 12/2016 | Felt et al. | |
| 9,883,951 B2 | 2/2018 | Lopez | |
| 10,413,427 B2* | 9/2019 | Trieu | A61F 2/447 |
| 10,603,185 B2* | 3/2020 | Hovorka | A61F 2/4611 |
| 2004/0143332 A1* | 7/2004 | Krueger | A61B 17/1604 |
| | | | 606/90 |
| 2004/0243240 A1* | 12/2004 | Beaurain | A61F 2/4425 |
| | | | 606/90 |
| 2005/0033438 A1* | 2/2005 | Schultz | A61F 2/4425 |
| | | | 623/17.15 |
| 2005/0234553 A1* | 10/2005 | Gordon | A61F 2/4425 |
| | | | 623/17.13 |
| 2006/0041314 A1* | 2/2006 | Millard | A61F 2/4425 |
| | | | 623/17.15 |
| 2006/0149372 A1 | 7/2006 | Paxson et al. | |
| 2006/0282020 A1* | 12/2006 | Bertagnoli | A61F 2/4684 |
| | | | 700/118 |
| 2008/0103596 A1* | 5/2008 | Shikinami | A61F 2/442 |
| | | | 623/17.15 |
| 2008/0109081 A1* | 5/2008 | Bao | A61F 2/4425 |
| | | | 623/47 |
| 2009/0088853 A1* | 4/2009 | Ogilvie | A61F 2/442 |
| | | | 623/17.11 |
| 2012/0083888 A1* | 4/2012 | Moumene | A61F 2/4425 |
| | | | 623/17.16 |
| 2012/0172990 A1* | 7/2012 | Kim | A61F 2/4425 |
| | | | 623/17.16 |
| 2013/0274880 A1* | 10/2013 | Arramon | A61F 2/4425 |
| | | | 623/17.15 |
| 2016/0074170 A1 | 3/2016 | Rogers et al. | |
| 2019/0008651 A1* | 1/2019 | Doty | A61F 2/4425 |
| 2019/0329544 A1* | 10/2019 | Yadin | B29C 64/153 |
| 2021/0267771 A1 | 9/2021 | Bray | |

FOREIGN PATENT DOCUMENTS

| | | |
|---|---|---|
| CN | 105708584 A | 6/2016 |
| CN | 107049563 A | 8/2017 |
| TW | 200722065 A | 6/2007 |
| TW | 200724116 A | 7/2007 |
| TW | I645842 B | 1/2019 |
| TW | I724962 | 4/2021 |

OTHER PUBLICATIONS

Othman, Yahya A., et al., Artificial disc replacement in spine surgery, Annals of Translational Medicine, Jun. 2019, 10 pages.

H, Anitha, et al., Automatic Quantification of Spinal Curvature in Scoliotic Radiograph using Image Processing, Jan. 26, 2011, J Med Syst (2012), 36:1943-1951.

Lauryssen, Carl, et al., Cervical total disc replacement using a novel compressible prosthesis: results from a prospective food and drug administration- regulated feasibility study with 24-month follow-up, International Journal of Spine Surgery 6 (2012) 71-77.

Lima, Mauricio Coelho et al., Parameters for the Evaluation of Cervical Sagittal Balance in Idiopathic Scoliosis, (UNICAMP) School of Medical Sciences, Spinal Surgery Group, Brazil, 2017: 16(1): 38-41.

Jacobs, Eva Md, Prediction of mechanical complications in adult spinal deformity surgery—the GAP score versus the Schwab classification, The Spine Journal, Nov. 28, 2018.

Yilgor, Caglar, MD, Relative lumbar lordosis and lordosis distribution index: individualized pelvic incidence-based proportional parameters that quantify lumbar lordosis more precisely than the concept of pelvic incidence minus lumbar ordosis, Neurosurg Focus 43 (6): E5, Dec. 2017.

Beltsios, Michail, Sagittal alignment of the cervical spine after neck injury, European Journal of Orthopaedic Surgery & Traumatology, Mar. 2012.

Stokes, Ian A.F., Three-dimensional terminology of spinal deformity. A report presented to the Scoliosis Research Society by the Scoliosis Research Society Working Group on 3-D terminology of spinal deformity, Spine, vol. 19, No. 2, pp. 236-248, 1994.

Van Den Eerenbeemt, Karin D. et al., Total disc replacement surgery for symptomatic degenerative lumbar disc disease: a systematic review of the literature, Eur Spine J (2010) 19:1262-1280.

TW Office Action dated Mar. 21, 2022 as received in Application No. 110145176.

* cited by examiner

ARTIFICIAL INTERVERTEBRAL DISC

CROSS-REFERENCE TO RELATED APPLICATIONS

This non-provisional application claims priority under 35 U.S.C. § 119(a) on Patent Application No(s). 110145176 filed in Taiwan, R.O.C. on Dec. 3, 2021, the entire contents of which are hereby incorporated by reference.

TECHNICAL FIELD

This disclosure relates to an artificial intervertebral disc.

BACKGROUND

Clinically, degenerative disc disease is usually treated by replacing degenerated intervertebral discs with artificial intervertebral disc implants. A conventional artificial intervertebral disc usually consists of three components which are an upper metal plate, a lower metal plate and a gasket. The upper metal plate is slidable on the gasket with a fixed radius, which is unable to reproduce the freedom of movement provided by natural intervertebral discs. Therefore, the conventional artificial intervertebral disc may overly wear down over a period of time. Moreover, after the partial disc replacement surgery for the spine, the original spine movement of patients may be compromised, and the life quality of the patients would be influenced due to the discomfort caused thereto.

SUMMARY

The present disclosure is to provide an artificial intervertebral disc, which is capable of reproducing the freedom of movement provided by natural intervertebral discs and preventing the artificial intervertebral disc from overly wearing down.

One embodiment of the disclosure provides an artificial intervertebral disc configured to be inserted between adjacent human vertebrae. The artificial intervertebral disc includes a first connection block, a joint block and a second connection block. The joint block has a convex surface and a rear surface. The rear surface of the joint block is stacked on the first connection block. The second connection block is slidably stacked on the convex surface of the joint block, such that the second connection block is movable relative to the first connection block. In addition, the convex surface is a curved surface, and the convex surface is arranged off-axis with respect to the rear surface.

BRIEF DESCRIPTION OF THE DRAWINGS

The present disclosure will become more fully understood from the detailed description given hereinbelow and the accompanying drawings which are given by way of illustration only and thus are not limitative of the present disclosure and wherein.

DETAILED DESCRIPTION

Aspects and advantages of the invention will become apparent from the following detailed descriptions with the accompanying drawings. For purposes of explanation, one or more specific embodiments are given to provide a thorough understanding of the invention, and which are described in sufficient detail to enable one skilled in the art to practice the described embodiments. It should be understood that the following descriptions are not intended to limit the embodiments to one specific embodiment. On the contrary, it is intended to cover alternatives, modifications, and equivalents as can be included within the spirit and scope of the described embodiments as defined by the appended claims.

Figure 1:
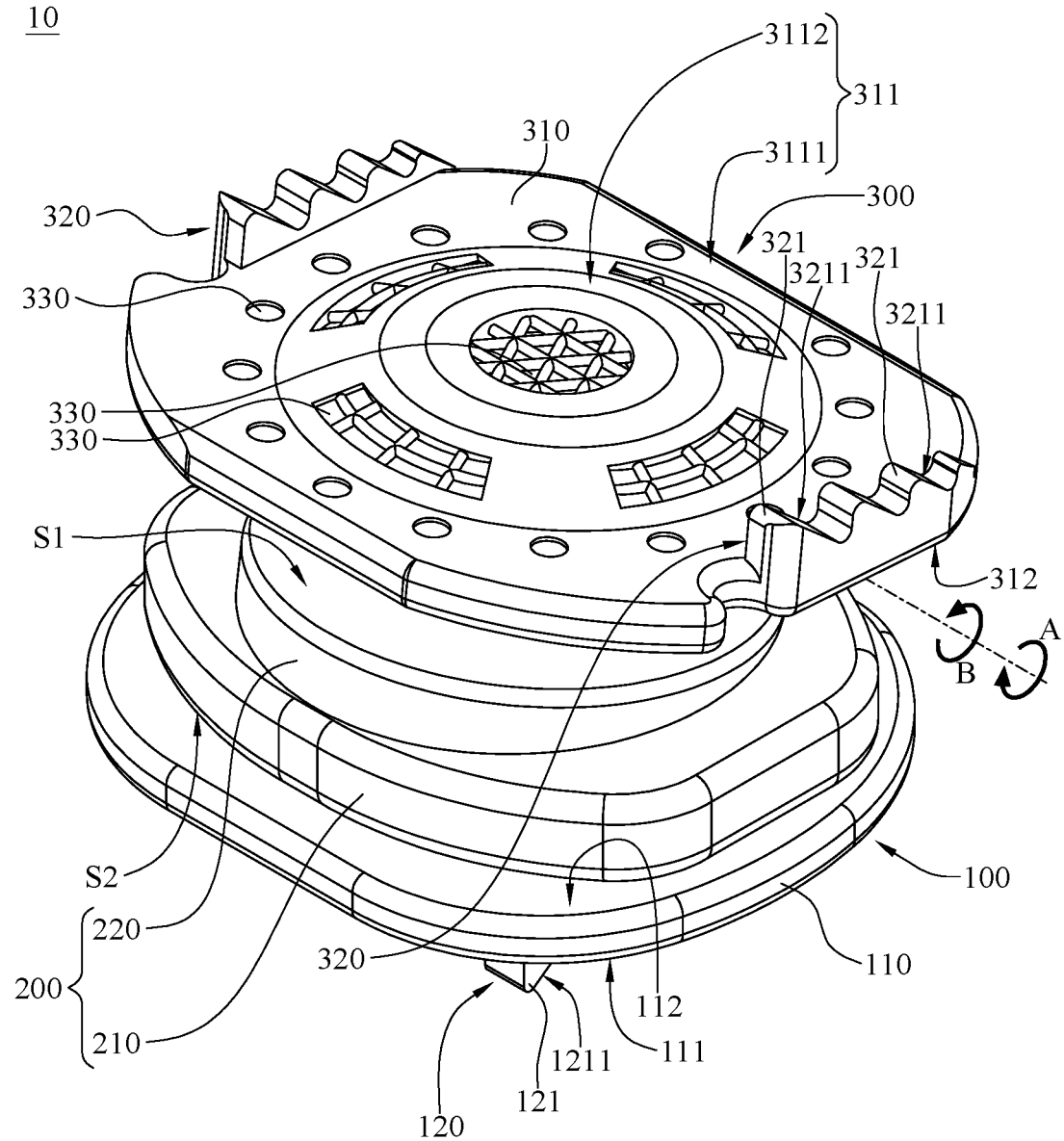
FIG. 1 is a perspective view of an artificial intervertebral disc in accordance with a first embodiment of the disclosure.
Figure 2:
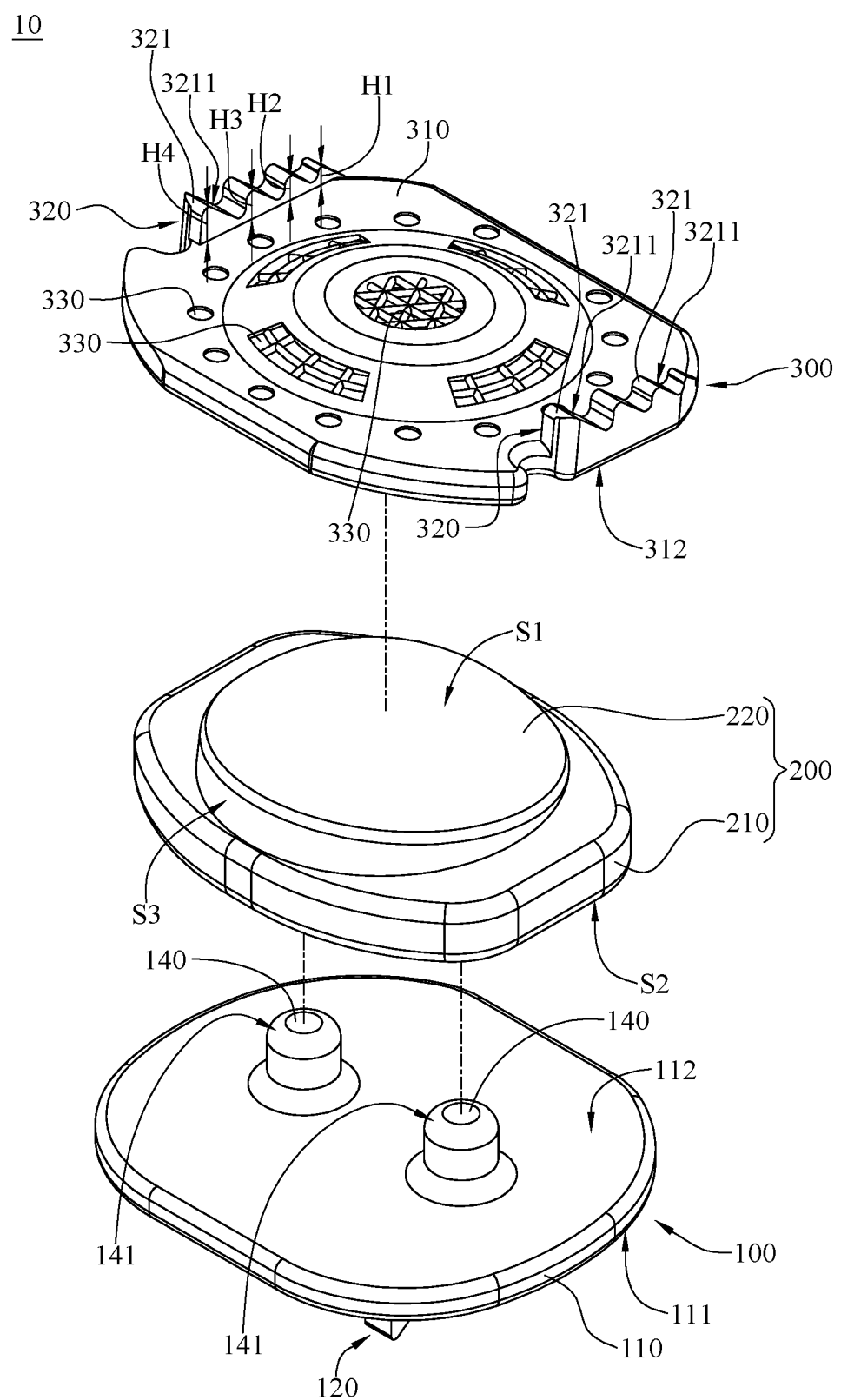
FIG. 2 is an exploded view of the artificial intervertebral disc in FIG. 1.
Figure 3:
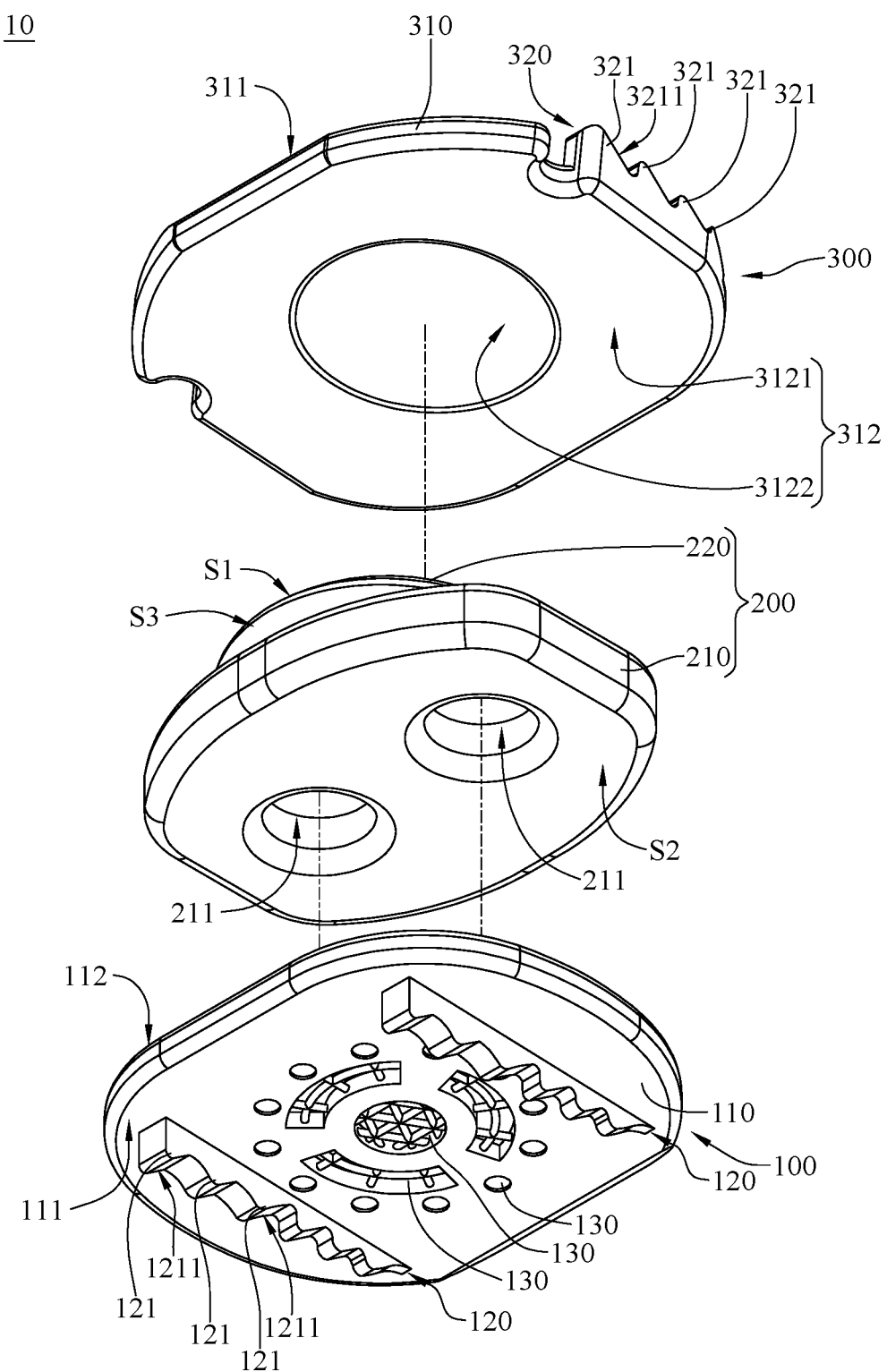
FIG. 3 is another exploded view of the artificial intervertebral disc in FIG. 1.
Figure 4:
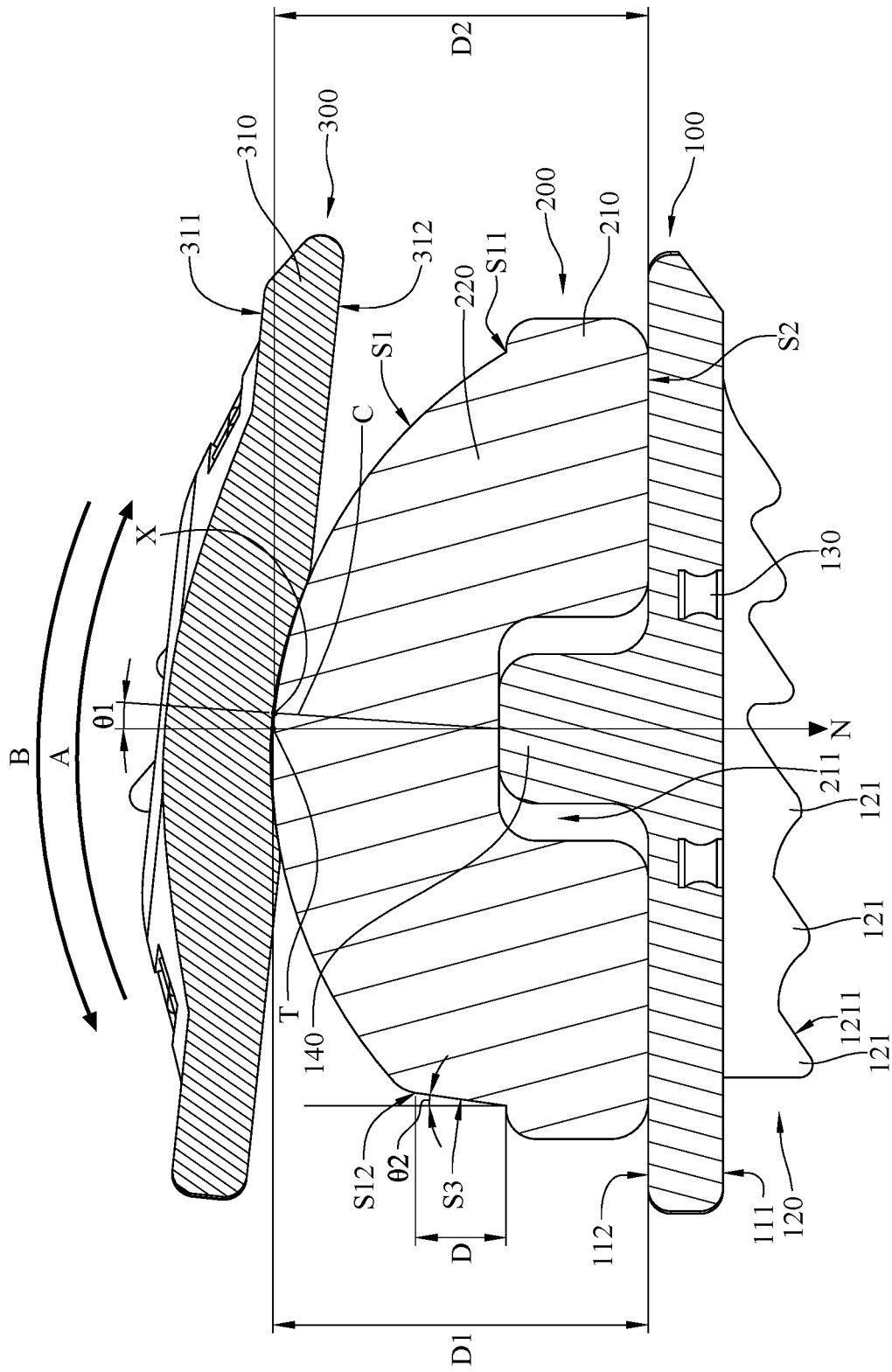
FIG. 4 is a cross-sectional view of the artificial intervertebral disc in FIG. 1.
Figure 5:
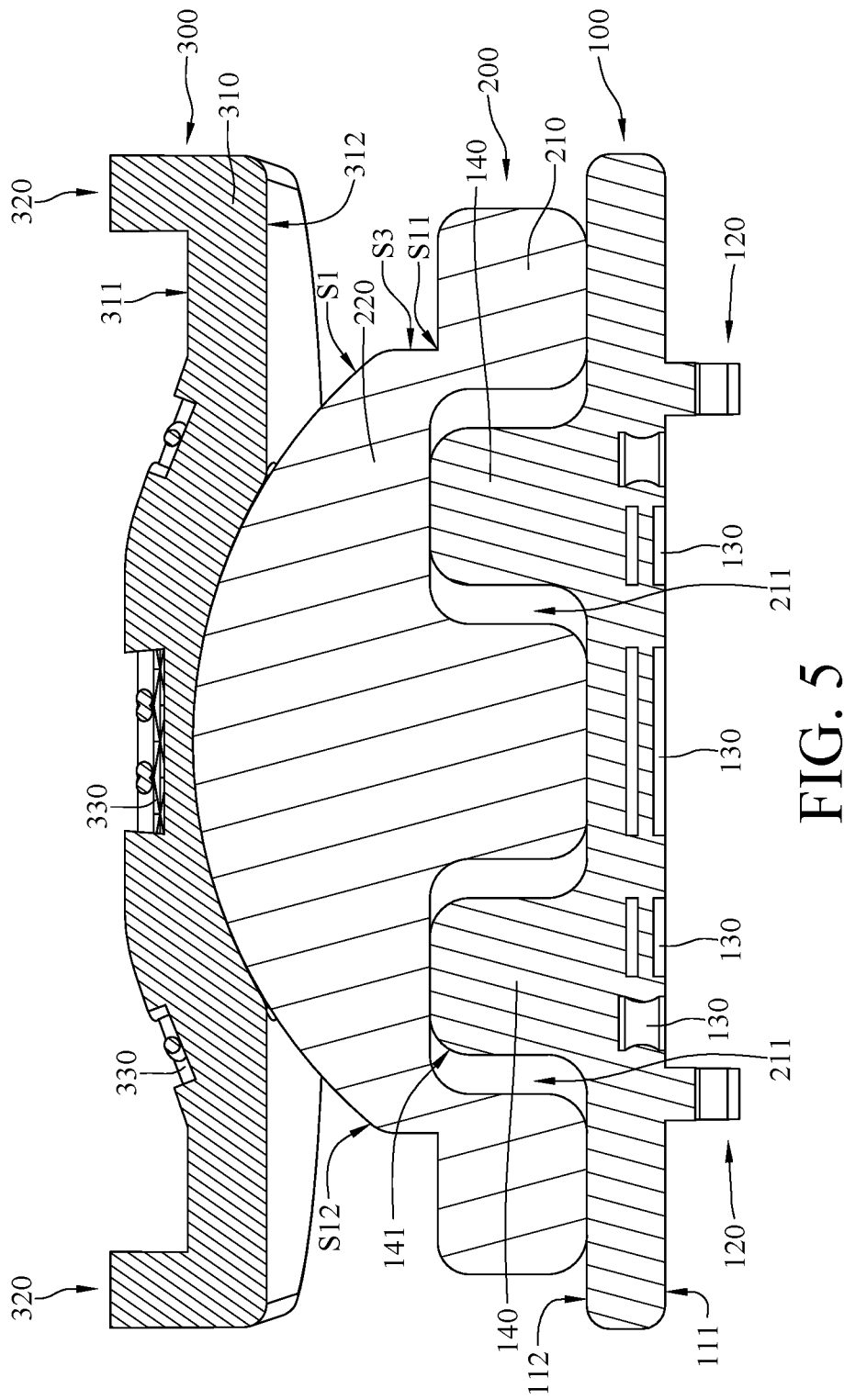
FIG. 5 is another cross-sectional view of the artificial intervertebral disc in FIG. 1.

Please refer to FIG. 1 to FIG. 5. FIG. 1 is a perspective view of an artificial intervertebral disc 10 in accordance with a first embodiment of the disclosure. FIG. 2 is an exploded view of the artificial intervertebral disc 10 in FIG. 1. FIG. 3 is another exploded view of the artificial intervertebral disc 10 in FIG. 1. FIG. 4 is a cross-sectional view of the artificial intervertebral disc 10 in FIG. 1. FIG. 5 is another cross-sectional view of the artificial intervertebral disc 10 in FIG. 1.

In this embodiment, the artificial intervertebral disc 10 is configured to be disposed between adjacent human vertebrae (not shown). The artificial intervertebral disc 10 includes a first connection block 100, a joint block 200 and a second connection block 300.

The first connection block 100 is configured to be connected to a vertebra, and the first connection block 100 is, for example, made of titanium alloy, cobalt-chromium-molybdenum alloy or stainless steel so as to increase the durability and structural strength of the first connection block 100. The first connection block 100 includes a first body portion 110 and two first convex-concave structures 120. The first body portion 110 has a first outer surface 111 and a first inner surface 112 located opposite to each other. The joint block 200 is stacked on the first inner surface 112 of the first body portion 110 of the first connection block 100. The two first convex-concave structures 120 protrude from the first outer surface 111 of the first body portion 110, and the two first convex-concave structures 120 are symmetrically arranged at two opposite sides of the first outer surface 111.

Figure 6:
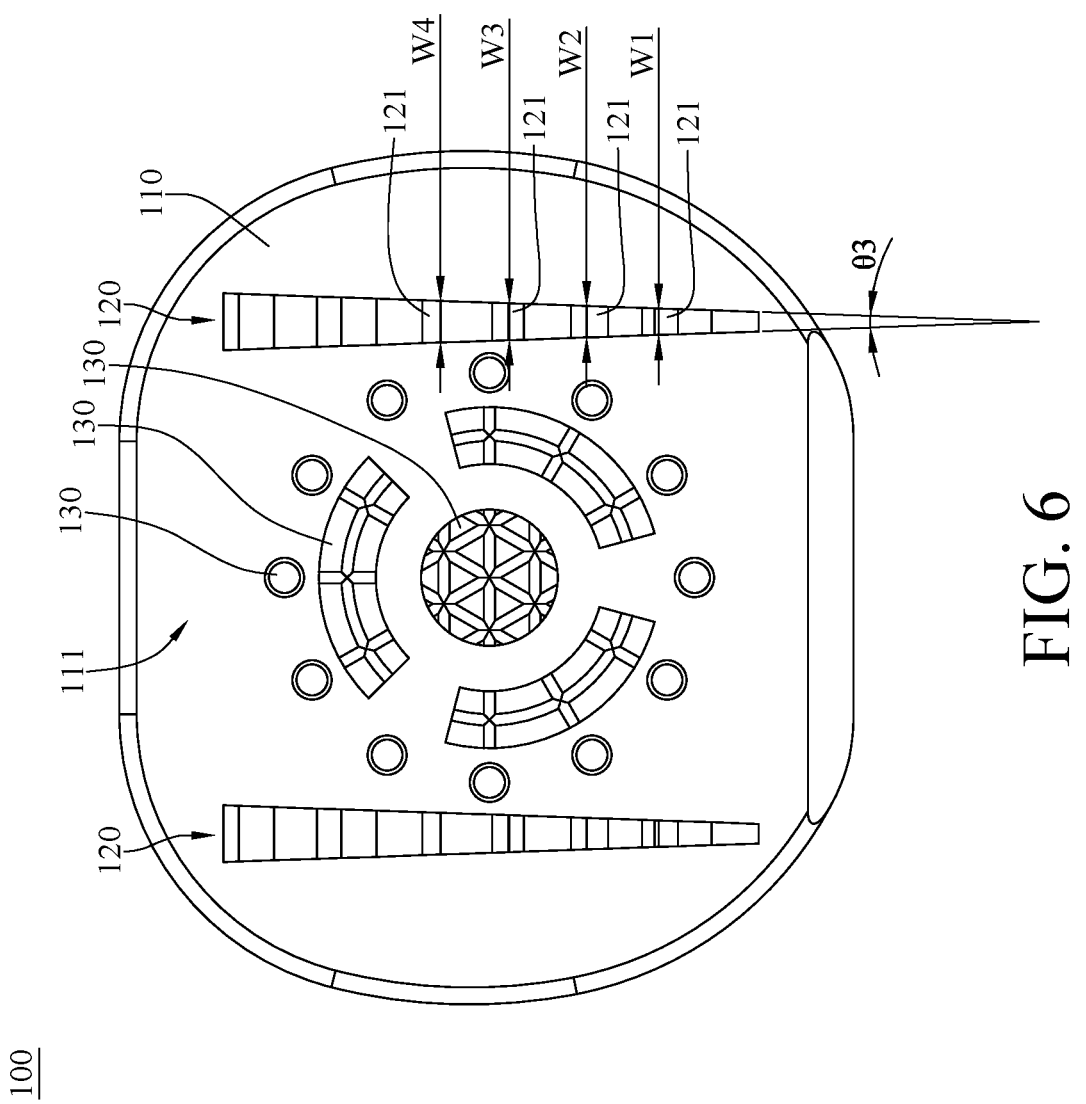
FIG. 6 is a bottom view of a first connection block of the artificial intervertebral disc in FIG. 1.

In this embodiment, each of the first convex-concave structures 120 is in a tapered shape (as shown in FIG. 6) and has hook-shaped parts, which is favorable for the first connection block 100 to be inserted between adjacent human vertebrae and prevents the first connection block 100 from detaching from the vertebrae.

In this embodiment, the two first convex-concave structures 120 are symmetrically arranged, but the present disclosure is not limited thereto. In other embodiments, two first convex-concave structures may be asymmetrically arranged. Furthermore, in this embodiment, the quantity of the first convex-concave structures 120 is two, but the present disclosure is not limited thereto. In other embodiments, the quantity of the first convex-concave structure may be one.

In this embodiment, the first body portion 110 may further have a plurality of first hole structures 130. The first hole structures 130 are, for example, in single hole type, lattice type, sponge type or wave shape type, and the first hole structures 130 are located at the first outer surface 111 of the first body portion 110 so as to enhance the integration of the first body portion 110 and the vertebra and reduce complications due to detachment of the first connection block 100. In this embodiment, a distribution percentage of the first hole structures 130 on the first outer surface 111 ranges, for example, from 20% to 80%, and a distribution density of the first hole structures 130 can be even or uneven (e.g., from loose to dense or from dense to loose). In addition, a diameter of each of the first hole structures 130 ranges, for example, from 0.3 mm to 0.6 mm.

Furthermore, a ratio of a distance between the first outer surface 111 having the first hole structures 130 and the first inner surface 112 being smooth to a thickness of the first connection block 100 ranges from 40% to 60%.

The joint block 200 is made of, for example and not limited to, ultra-high-molecular-weight polyethylene (UHMWPE), polyether ether ketone (PEEK) or polyphenylsulfone (PPSU), and the joint block 200 has a convex surface S1 and a rear surface S2. In detail, the joint block 200 includes a base portion 210 and a protrusion portion 220. The protrusion portion 220 protrudes from the base portion 210. The rear surface S2 is located at one side of the base portion 210 located away from the protrusion portion 220, and the rear surface S2 of the joint block 200 is stacked on the first connection block 100. The convex surface S1 is located at one side of the protrusion portion 220 located away from the base portion 210. In this embodiment, the joint block 200 may further have a connection surface S3. One side S11 of the convex surface S1 is connected to the base portion 210, and an opposite side S12 of the convex surface S1 is connected to the base portion 210 via the connection surface S3, such that distances from two opposite sides of the convex surface S1 to the base portion 210 are different from each other. In this embodiment, a distance from the side S11 of the convex surface S1 to the base portion 210 is zero, a distance D from the side S12 of the convex surface S1 to the base portion 210 is larger than zero, but the present disclosure is not limited thereto. In other embodiments, distances from two opposite sides of a convex surface to a base portion may be both larger than zero and different from each other.

In this embodiment, the convex surface S1 is a curved surface, and the convex surface S1 is arranged off-axis with respect to the rear surface S2. Therefore, the artificial intervertebral disc 10 is capable of providing a patient with optimal joint motion angle and lower stress concentration, thereby minimizing the damage due to wearing down. Said "arranged off-axis" means that, for example, an angle $\theta 1$ between a central axis C of the convex surface S1 and a normal line N of the rear surface S2 is larger than 0 degree, and an angle $\theta 2$ between the connection surface S3 and the normal line N of the rear surface S2 is larger than 0 degree. In this embodiment, the angle $\theta 2$ between the connection surface S3 and the normal line N of the rear surface S2 is equal to the angle $\theta 1$ between the central axis C of the convex surface S1 and the normal line N of the rear surface S2, but the present disclosure is not limited thereto. In other embodiments, an angle between a connection surface and a normal line of a rear surface may not be equal to an angle between a central axis of a convex surface and the normal line of the rear surface. Moreover, a radius of the convex surface ranges, for example, from 6 mm to 10 mm. Therefore, the usage times thereof can be increased before fatigue failure occurs.

Additionally, said "arranged off-axis" further means that, for example, a distance D1 from a vertex T of the convex surface S1 to the rear surface S2 is different from a distance D2 from an intersection point X of the central axis C and the convex surface S1 to the rear surface S2.

Moreover, when a position of the joint block 200 is consistent with a natural position of the human spine, the artificial intervertebral disc 10 can provide the patient with an optimal motion angle, so the inclined angle of the convex surface S1 of the joint block 200 may be customized according to the natural position of patient's spine. In practice, during the custom manufacturing of the artificial intervertebral disc 10, the manufacturer may obtain the information of the natural position of the patient's spine, and then, determine an ideal inclined angle value (e.g., 2, 5 or 8 degrees) of the convex surface S1 of the joint block 200 based on the natural position of the patient's spine. By doing so, the customized artificial intervertebral disc 10 may provide a wider bending range. For example, a revolving angle of the second connection block 300 relative to the first connection block 100 is, for example, around 30 degrees in an off-axis flexion direction (e.g., direction B) and an off-axis extension direction (e.g., direction A). When the artificial intervertebral disc 10 bends forwards in the off-axis extension direction (e.g., direction A), an average stress in the artificial intervertebral disc 10 is smaller than an average stress in a conventional artificial intervertebral disc (which is not arranged off-axis). When the artificial intervertebral disc 10 stretches backwards in the off-axis flexion direction (e.g., direction B), an average stress in a part of the base portion 210 of the joint block 200 is larger than the average stress in the conventional artificial intervertebral disc (which is not arranged off-axis), but an average stress in the protrusion portion 220 of the joint block 200 is smaller than the average stress in the conventional artificial intervertebral disc (which is not arranged off-axis). Since the wearing down of the joint block 200 mainly occurs on the protrusion portion 220, relatively small average stress in the protrusion portion 220 of the joint block 200 is favorable for the extension of service life of the artificial intervertebral disc 10.

In this embodiment, the base portion 210 of the joint block 200 has two recesses 211 located at the rear surface S2 of the base portion 210. The first connection block 100 further includes two positioning protrusions 140 protruding from the first inner surface 112 of the first body portion 110, and the two positioning protrusions 140 are at least partially located at the two recesses 211, respectively. Furthermore, each of the positioning protrusions 140 is, for example, a cylinder (i.e., in a cylindrical shape), and the positioning protrusions 140 has a fillet structure 141 at one side thereof in contact with the joint block 200. The positioning protrusions 140 are configured to prevent excessive displacement of the artificial intervertebral disc 10 and ensure intact annular periphery of the intervertebral disc. Furthermore, in this embodiment, a diameter of each of the positioning protrusions 140 ranges, for example, from 2 mm to 6 mm.

In this embodiment, the periphery of the joint block 200 is surrounded by a biomimetic annulus fibrosus. The structure of the biomimetic annulus fibrosus is intact, and there is no defect. The periphery of the joint block 200 is fully covered by the biomimetic annulus fibrosus, which is similar to the manner of a natural annulus fibrosus fully surrounding the soft inner core and nucleus pulposus of the intervertebral disc. Said "intact structure of the biomimetic annulus fibrosus" means that there is no breach at the periphery of the joint block 200. Additionally, the joint block 200 is designed to have smooth surfaces so as to increase the abrasion resistance of the joint block 200.

The second connection block 300 is slidably stacked on the convex surface S1 of the joint block 200, such that the second connection block 300 is movable relative to the first connection block 100; that is, the second connection block 300 can bend forwards or backwards with respect to the first connection block 100. In detail, the second connection block 300 is connected to a vertebra, and the second connection block 300 is made of, for example and not limited to, titanium alloy, cobalt-chromium-molybdenum alloy or stainless steel so as to increase the durability and structural strength of the second connection block 300. The second connection block 300 includes a second body portion 310 and two second convex-concave structures 320. The second body portion 310 has a second outer surface 311 and a second inner surface 312 located opposite to each other. The second outer surface 311 has a planar part 3111 and a protrusion part 3112, and the planar part 3111 surrounds the protrusion part 3112. The second inner surface 312 has a planar part 3121 and a recess part 3122, and the planar part 3121 surrounds the recess part 3122.

The second inner surface 312 of the second body portion 310 of the second connection block 300 is stacked on the joint block 200, such that the convex surface S1 of the joint block 200 is in contact with the recess part 3122 of the second inner surface 312. The two second convex-concave structures 320 protrude from the planar part 3111 of the second outer surface 311 of the second body portion 310, and the two second convex-concave structures 320 are symmetrically located at two opposite sides of the second outer surface 311. Furthermore, a ratio of a height H of each of the second convex-concave structures 320 to a thickness T of the second connection block 300 is, for example, 0.5.

In this embodiment, each of the second convex-concave structures 320 is in a tapered shape and has hook-shaped parts, which is favorable for the second connection block 300 to be inserted between adjacent human vertebrae and prevents the second connection block 300 from detaching from the vertebrae.

In this embodiment, the two second convex-concave structures 320 are symmetrically arranged, but the present disclosure is not limited thereto. In other embodiments, two second convex-concave structures may be asymmetrically arranged. Furthermore, in this embodiment, the quantity of the second convex-concave structures 320 is two, but the present disclosure is not limited thereto. In other embodiments, the quantity of the second convex-concave structure may be one.

In this embodiment, the second body portion 310 may further have a plurality of second hole structures 330. The second hole structures 330 are, for example, in single hole type, lattice type, sponge type or wave shape type, and the second hole structures 330 are located at the planar part 3111 and the protrusion part 3112 of the second outer surface 311 of the second body portion 310 so as to enhance the integration of the second body portion 310 and the vertebra and reduce complications due to detachment of the second connection block 300. In this embodiment, a distribution percentage of the second hole structures 330 on the second outer surface 311 ranges, for example, from 20% to 80%, and a distribution density of the second hole structures 330 can be even or uneven (e.g., from loose to dense or from dense to loose). In addition, a diameter of each of the second hole structures 330 ranges, for example, from 0.3 mm to 0.6 mm.

Figure 7:
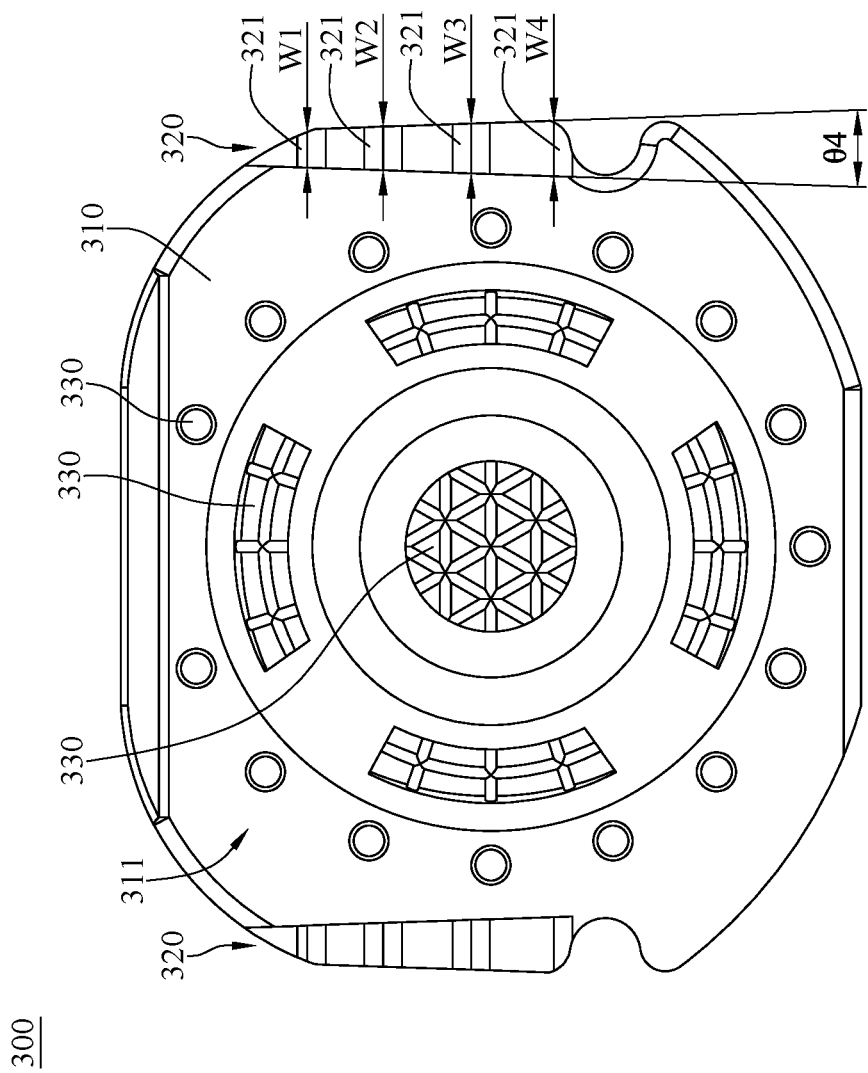
FIG. 7 is a top view of a second connection block of the artificial intervertebral disc in FIG. 1.

Please refer to FIG. 6 and FIG. 7. FIG. 6 is a bottom view of the first connection block 100 of the artificial intervertebral disc 10 in FIG. 1. FIG. 7 is a top view of the second connection block 300 of the artificial intervertebral disc 10 in FIG. 1.

In this embodiment, each of the first convex-concave structures 120 includes a plurality of first engagement parts 121 (e.g., hook-shaped parts), and each of the second convex-concave structures 320 includes a plurality of second engagement parts 321 (e.g., hook-shaped parts). Widths W1-W4 of the first engagement parts 121 increases sequentially and a taper angle θ3 of each of the first convex-concave structures 120 ranges, for example, from 2 degrees to 8 degrees, and widths W1-W4 of the second engagement parts 321 increases sequentially and a taper angle θ4 of each of the second convex-concave structures 320 ranges, for example, from 2 degrees to 8 degrees.

Figure 8:
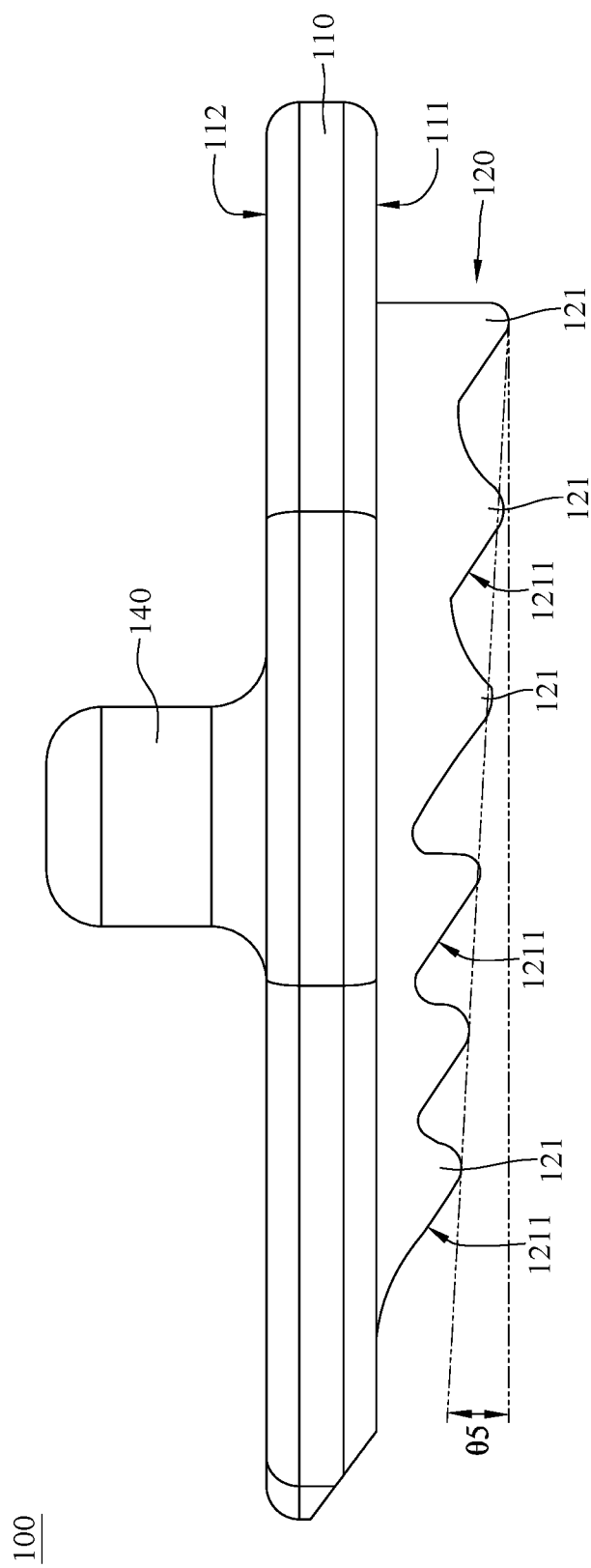
FIG. 8 is a side view of the first connection block in FIG. 1.
Figure 9:
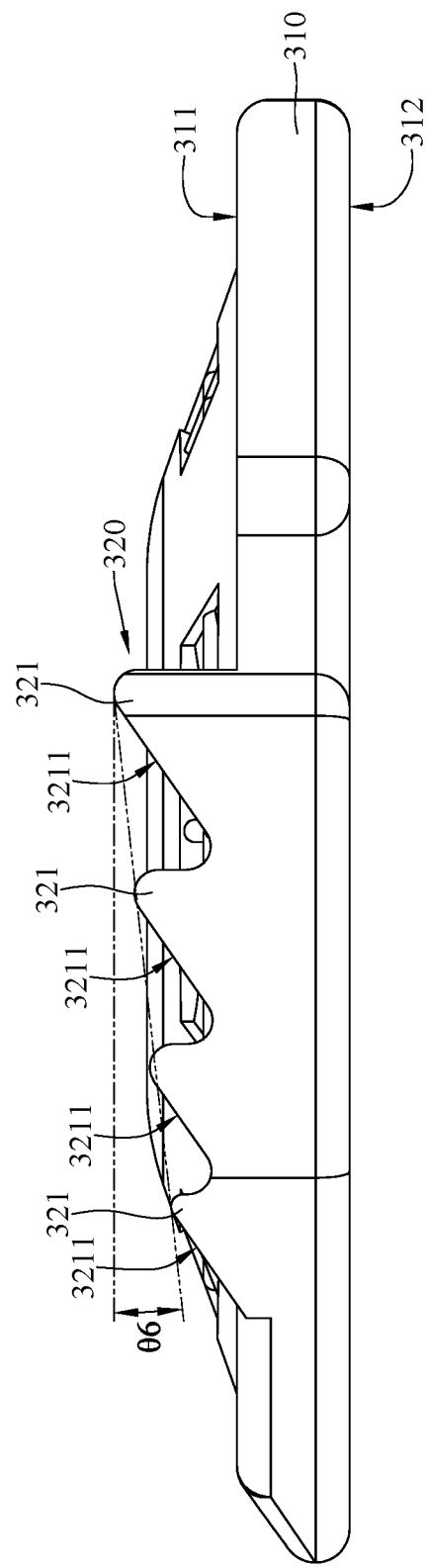
FIG. 9 is a side view of the second connection block in FIG. 1.

Please refer to FIG. 8 and FIG. 9. FIG. 8 is a side view of the first connection block 100 in FIG. 1. FIG. 9 is a side view of the second connection block 300 in FIG. 1. In this embodiment, each of the first convex-concave structures 120 includes a plurality of first engagement parts 121 (e.g., hook-shaped parts), and each of the first engagement parts 121 has a first inclined surface 1211. Each of the second convex-concave structures 320 includes a plurality of second engagement parts 321 (e.g., hook-shaped parts), and each of the second engagement parts 321 has a second inclined surface 3211. Heights H1-H4 of the first engagement parts 121 and the second engagement parts 321 increases sequentially, and the heights H1-H4 ranges, for example, from 1 mm to 3 mm, such that an inclined angle θ5 of the first engagement parts 121 and an inclined angle θ6 of the second engagement parts 321 range from 1 degree to 5 degrees. Therefore, the first connection block 100 and the second connection block 300 can be more easily installed between the vertebrae via the engagement parts with sequentially increasing heights.

Figure 10:
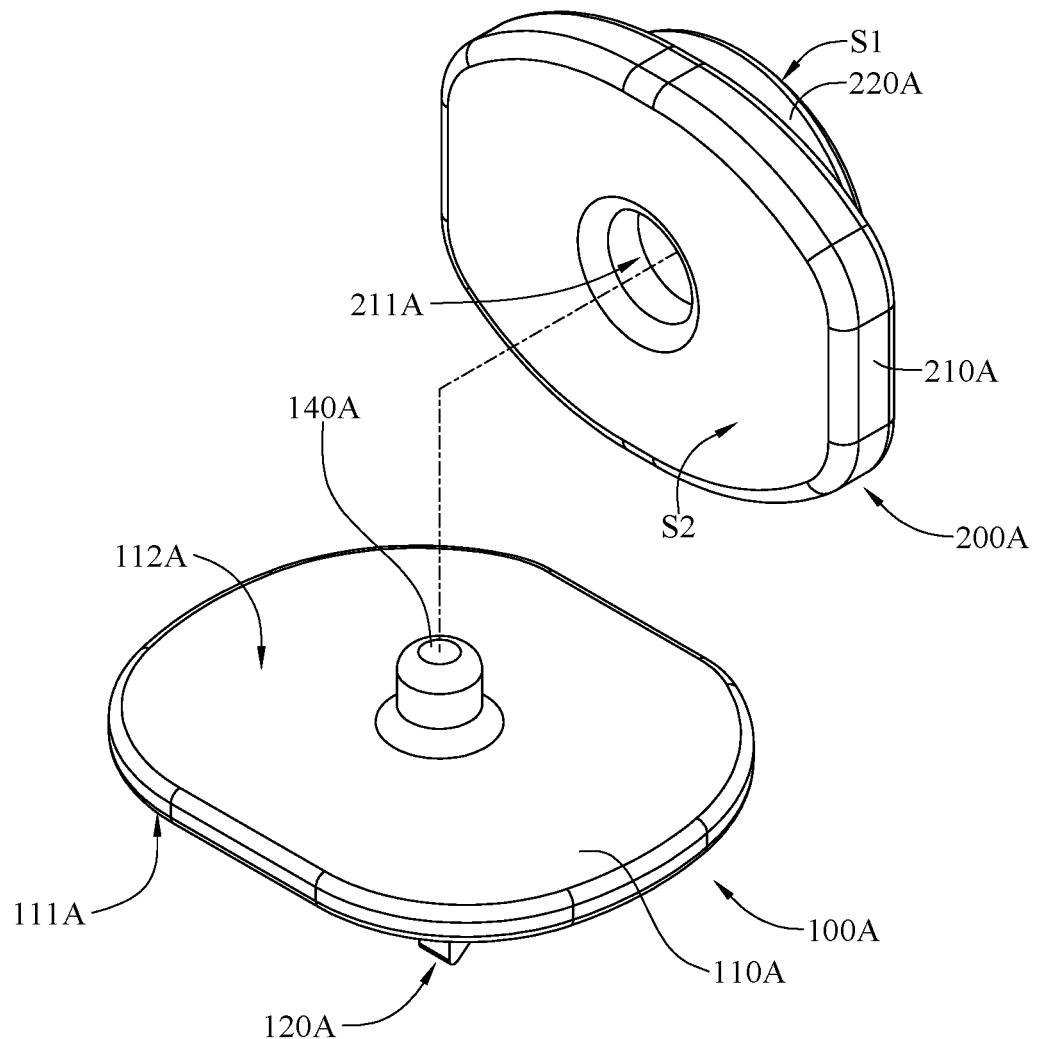
FIG. 10 is an exploded view of a first connection block and a joint block in accordance with a second embodiment of the disclosure.
Figure 11:
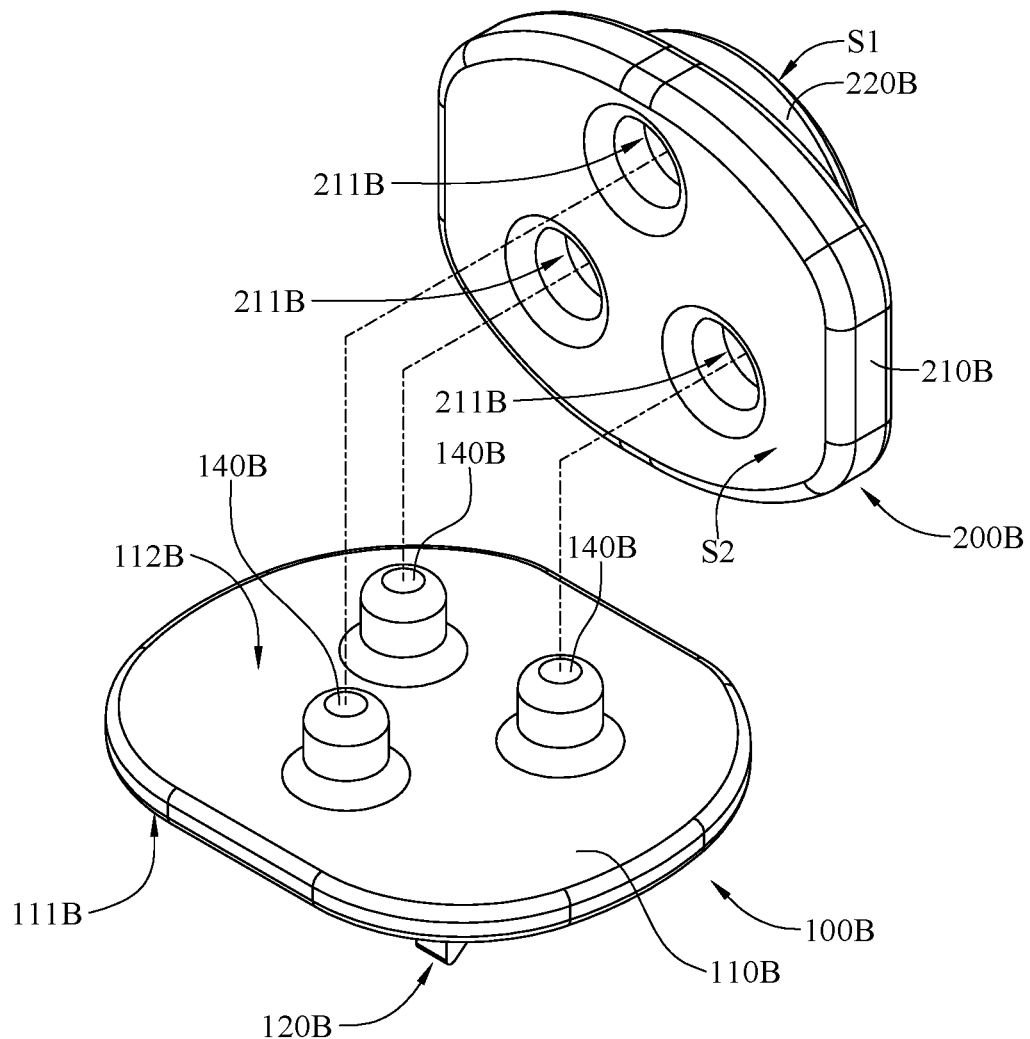
FIG. 11 is an exploded view of a first connection block and a joint block in accordance with a third embodiment of the disclosure.
Figure 12:
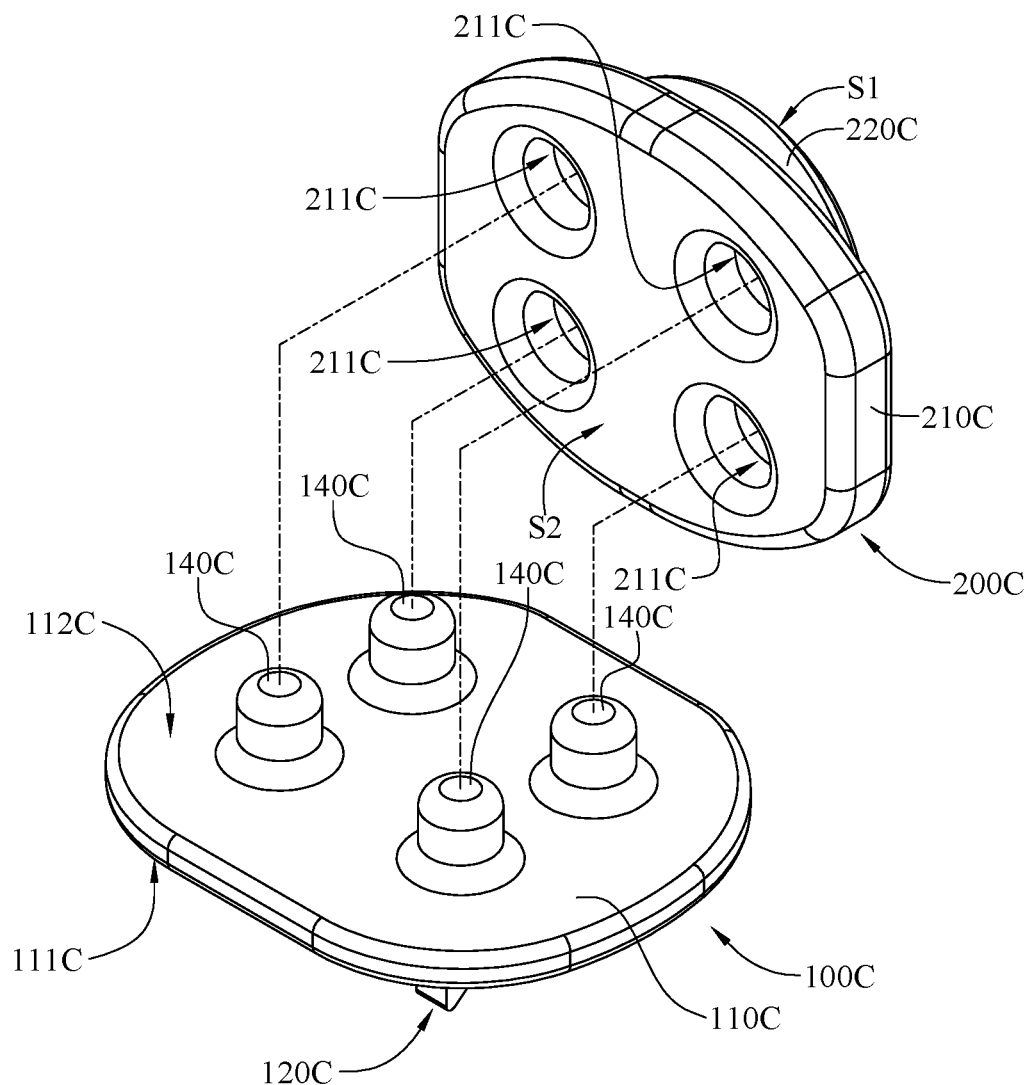
FIG. 12 is an exploded view of a first connection block and a joint block in accordance with a fourth embodiment of the disclosure.

The quantity of the aforementioned positioning protrusions is two, but the present disclosure is not limited thereto. Please refer to FIG. 10 to FIG. 12. FIG. 10 is an exploded view of a first connection block 100A and a joint block 200A in accordance with a second embodiment of the disclosure. FIG. 11 is an exploded view of a first connection block 100B and a joint block 200B in accordance with a third embodiment of the disclosure. FIG. 12 is an exploded view of a first connection block 100C and a joint block 200C in accordance with a fourth embodiment of the disclosure.

As shown in FIG. 10, the first connection block 100A includes a first body portion 110A, a first convex-concave structure 120A and one positioning protrusion 140A. The first body portion 110A has a first outer surface 111A and a first inner surface 112A. The first convex-concave structure 120A protrudes from the first outer surface 111A. The positioning protrusion 140A protrudes from the first inner surface 112A. The joint block 200A includes a base portion 210A and a protrusion portion 220A. The protrusion portion 220A protrudes from one side of the base portion 210A, the protrusion portion 220A has a convex surface S1 at one side thereof located away from the base portion 210A, and the base portion 210A has a rear surface S2 at one side thereof located away from the protrusion portion 220A. The base portion 210A of the joint block 200A has one recess 211A configured for the positioning protrusion 140A to be disposed therein so as to prevent excessive displacement of the artificial intervertebral disc.

As shown in FIG. 11, the first connection block 100B includes a first body portion 110B, a first convex-concave structure 120B and three positioning protrusions 140B. The first body portion 110B has a first outer surface 111B and a first inner surface 112B. The first convex-concave structure 120B protrudes from the first outer surface 111B. The positioning protrusions 140B protrudes from the first inner surface 112B. The joint block 200B includes a base portion 210B and a protrusion portion 220B. The protrusion portion 220B protrudes from one side of the base portion 210B, the protrusion portion 220B has a convex surface S1 at one side thereof located away from the base portion 210B, and the base portion 210B has a rear surface S2 at one side thereof located away from the protrusion portion 220B. The base portion 210B of the joint block 200B has three recesses 211B configured for the positioning protrusions 140B to be respectively disposed therein so as to prevent excessive displacement of the artificial intervertebral disc.

As shown in FIG. 12, the first connection block 100C includes a first body portion 110C, a first convex-concave structures 120C and four positioning protrusions 140C. The first body portion 110C has a first outer surface 111C and a first inner surface 112C. The first convex-concave structures 120C protrudes from the first outer surface 111C. The positioning protrusions 140C protrudes from the first inner surface 112C. The joint block 200C includes a base portion 210C and a protrusion portion 220C. The protrusion portion 220C protrudes from one side of the base portion 210C, the protrusion portion 220C has a convex surface S1 at one side thereof located away from the base portion 210C, and the base portion 210C has a rear surface S2 at one side thereof located away from the protrusion portion 220C. The base portion 210C of the joint block 200C has four recesses 211C configured for the positioning protrusions 140C to be respectively disposed therein so as to prevent excessive displacement of the artificial intervertebral disc.

In view of the above description, the convex surface is arranged off-axis with respect to the rear surface, such that the artificial intervertebral disc is capable of providing the patient with optimal joint motion angle and lower stress concentration, thereby minimizing the material damage due to wearing down.

Furthermore, each of the convex-concave structures of the connection blocks is in a tapered shape and has hook-shaped parts, which is favorable for the connection blocks to be inserted between the vertebrae and prevents the connection blocks from detaching from the vertebrae.

Moreover, the hole structures of the connection blocks are configured to enhance the integration of the connection blocks and the vertebra and reduce complications due to detachment of the connection blocks.

In addition, the positioning protrusion is configured to prevent excessive displacement of the artificial intervertebral disc and ensure intact annular periphery of the intervertebral disc.

Additionally, the joint block is designed to have smooth surfaces so as to increase the abrasion resistance of the joint block.

The embodiments were chosen and described in order to best explain the principles of the disclosure and its practical applications, to thereby enable others skilled in the art to best utilize the disclosure and various embodiments with various modifications as are suited to the particular use contemplated. It is intended that the scope of the disclosure be defined by the following claims and their equivalents.

What is claimed is:

1. An artificial intervertebral disc configured to be inserted between adjacent human vertebrae, and the artificial intervertebral disc comprising:
   a first connection block;
   a joint block having a convex surface and a rear surface, wherein the rear surface of the joint block is stacked on the first connection block; and
   a second connection block slidably stacked on the convex surface of the joint block, such that the second connection block is movable relative to the first connection block;
   wherein the convex surface is a spherical curved surface having a fixed radius of curvature, and the convex surface is arranged off-axis with respect to the rear surface;
   wherein the joint block comprises a base portion and a protrusion portion, the protrusion portion protrudes from the base portion, the rear surface is located at one side of the base portion located away from the protrusion portion, the convex surface is located at one side of the protrusion portion located away from the base portion, and distances from two opposite sides of the convex surface to the base portion are different from each other;
   wherein the joint block further has a connection surface, one side of the convex surface is connected to the base portion, and an opposite side of the convex surface is connected to the base portion via the connection surface;
   wherein an angle between the connection surface and a normal line of the rear surface is equal to an angle between a central axis of the convex surface and the normal line of the rear surface.

2. The artificial intervertebral disc according to claim 1, wherein the angle between the central axis of the convex surface and the normal line of the rear surface is larger than 0 degree.

3. The artificial intervertebral disc according to claim 2, wherein a radius of the convex surface ranges from 6 mm to 10 mm.

4. The artificial intervertebral disc according to claim 2, wherein a distance from a vertex of the convex surface to the rear surface is different from a distance from an intersection point of the central axis and the convex surface to the rear surface.

5. The artificial intervertebral disc according to claim 1, wherein the angle between the connection surface and the normal line of the rear surface is larger than 0 degree.

6. The artificial intervertebral disc according to claim 1, wherein the first connection block comprises a first body portion and at least one first convex-concave structure, the first body portion has a first outer surface and a first inner surface located opposite to each other, the joint block is stacked on the first inner surface of the first body portion of the first connection block, the at least one first convex-concave structure protrudes from the first outer surface of the first body portion, the second connection block comprises a second body portion and at least one second convex-concave structure, the second body portion has a second outer surface and a second inner surface located opposite to each other, the second inner surface of the second body portion of the second connection block is stacked on the joint block, and the at least one second convex-concave structure protrudes from the second outer surface of the second body portion.

7. The artificial intervertebral disc according to claim 6, wherein the at least one first convex-concave structure comprises a plurality of first engagement parts, heights of the plurality of first engagement parts increases sequentially, the at least one second convex-concave structure comprises a plurality of second engagement parts, and heights of the plurality of second engagement parts increases sequentially.

8. The artificial intervertebral disc according to claim 6, wherein the at least one first convex-concave structure comprises a plurality of first engagement parts, widths of the plurality of first engagement parts increases sequentially, the at least one second convex-concave structure comprises a plurality of second engagement parts, and widths of the plurality of second engagement parts increases sequentially.

9. The artificial intervertebral disc according to claim 6, wherein the second inner surface has a planar part and a recess part, the planar part surrounds the recess part, the convex surface is in contact with the recess part of the second inner surface.

10. The artificial intervertebral disc according to claim 6, wherein the base portion of the joint block has at least one recess, the at least one recess is located at the rear surface of the base portion, the first connection block further comprises at least one positioning protrusion, the at least one positioning protrusion protrudes from the first inner surface of the first body portion, and the at least one positioning protrusion is at least partially located in the at least one recess.

11. The artificial intervertebral disc according to claim 10, wherein the at least one positioning protrusion is a cylinder, and the at least one positioning protrusion has a fillet structure at one side thereof in contact with the joint block.

12. The artificial intervertebral disc according to claim 6, wherein the second outer surface has a planar part and a protrusion part, the planar part surrounds the protrusion part, the first body portion has a plurality of first hole structures, the plurality of first hole structures are located at the first outer surface of the first body portion, the second body portion has a plurality of second hole structures, the plurality of second hole structures are located at the planar part and the protrusion part of the second outer surface of the second body portion, and the at least one second convex-concave structure protrudes from the planar part of the second outer surface.

13. The artificial intervertebral disc according to claim 12, wherein a distribution percentage of the plurality of the first hole structures on the first outer surface ranges from 20% to 80%, and a distribution percentage of the plurality of second hole structures on the second outer surface ranges from 20% to 80%.

14. The artificial intervertebral disc according to claim 12, wherein a diameter of each of the plurality of first hole structures ranges from 0.3 mm to 0.6 mm, and a diameter of each of the plurality of second hole structures ranges from 0.3 mm to 0.6 mm.

15. The artificial intervertebral disc according to claim 6, wherein a ratio of a distance between the first outer surface and the first inner surface to a thickness of the first connection block ranges from 40% to 60%.

16. The artificial intervertebral disc according to claim 1, wherein the first connection block and the second connection block are made of titanium alloy, cobalt-chromium-molybdenum alloy or stainless steel, and the joint block is made of UHMWPE, PEEK or PPSU.

* * * * *